(12) United States Patent
Yuka et al.

(10) Patent No.: US 7,776,615 B2
(45) Date of Patent: Aug. 17, 2010

(54) METHOD FOR SOLID-PHASE MICRO EXTRACTION AND APPARATUS THEREFOR

(75) Inventors: Hiramatsu Yuka, Saitama (JP); Yamasaki Kazuhiko, Saitama (JP); Furuno Masahiro, Saitama (JP)

(73) Assignee: GL Sciences, Inc. (JP)

( * ) Notice: Subject to any disclaimer, the term of this patent is extended or adjusted under 35 U.S.C. 154(b) by 1251 days.

(21) Appl. No.: 10/475,471

(22) PCT Filed: Apr. 19, 2002

(86) PCT No.: PCT/JP02/03912

§ 371 (c)(1), (2), (4) Date: Apr. 26, 2004

(87) PCT Pub. No.: WO02/086488

PCT Pub. Date: Oct. 31, 2002

(65) Prior Publication Data

US 2008/0064115 A1    Mar. 13, 2008

(30) Foreign Application Priority Data

Apr. 20, 2001 (JP) .............................. 2001-122375

(51) Int. Cl.
- *G01N 1/18* (2006.01)
- *G01N 30/00* (2006.01)
- *B01D 15/00* (2006.01)

(52) U.S. Cl. .................... 436/178; 436/161; 422/50; 422/69; 422/261

(58) Field of Classification Search ............. 422/30, 422/68.1, 70, 89, 100, 101, 261, 69, 50; 436/178, 436/161

See application file for complete search history.

(56) References Cited

U.S. PATENT DOCUMENTS

| | | | |
|---|---|---|---|
| 5,565,622 A | 10/1996 | Murphy | |
| 5,691,206 A * | 11/1997 | Pawliszyn | .................... 436/178 |
| 6,164,144 A * | 12/2000 | Berg | ........................ 73/863.21 |
| 6,481,301 B2 * | 11/2002 | Pawliszyn | ................ 73/864.71 |
| 2003/0021730 A1 * | 1/2003 | Muller et al. | ............... 422/68.1 |
| 2005/0014156 A1 * | 1/2005 | Pawliszyn | ....................... 435/6 |

FOREIGN PATENT DOCUMENTS

| | | |
|---|---|---|
| EP | 1033169 | 9/2000 |
| WO | 9922244 | 5/1999 |

* cited by examiner

*Primary Examiner*—Jill Warden
*Assistant Examiner*—Dwan A Gerido
(74) *Attorney, Agent, or Firm*—Hahn Loeser + Parks LLP; Scott M. Oldham, Esq.

(57) ABSTRACT

The present invention is directed to a system for pre-treatment of a sample to be introduced in a chromatograph, and a method for performing solid-phase extraction of a component present in a sample. The system uses a syringe having a needle being provided with a porous body having a monolithic structure along at least an appropriate length of the needle and across an overall diameter of the needle. The method includes the steps of inserting the needle into the sample, passing the sample through the needle to retain an analyte within the porous body, and desorbtion of the retained analyte from the porous body.

11 Claims, 10 Drawing Sheets

METHOD FOR SOLID-PHASE MICRO EXTRACTION AND APPARATUS THEREFOR

TECHNICAL FIELD

The present invention relates to a method and apparatus for solid-phase-micro extraction, and particularly relates to a treating method and apparatus effective for a pre-treatment of a sample which is introduced to a chromatograph.

BACKGROUND ART

In a chromatographic analysis, it has been said that the time and effort required for the so-called pre-treatment, including sampling, extraction of an analyte, and sample preparation such as concentration represents 80% of the analytical work. Solid-Phase-Micro extraction (SPME) developed by Pawliszyn in 1990 is a method for pre-treating a sample, where such works and introduction into the chromatograph can be simply performed. In the SPME method, a fiber whose surface is coated with a liquid phase is exposed to a headspace or a solution of the sample in order to perform extraction, and an analyte extracted into the fiber liquid phase is thermally desorbed at a injection port during GC and is introduced to the GC (Japanese Patent Laid-Open No. 5-506715).

In addition, an In-tube SPME method in which a capillary column of GC is used for an adsorption mechanism (Hiroyuki Katayama, Shizuo Narimatsu, Heather L Lord, J. Pawliszyn Chromatography 20 (1999) 237-249) has been used recently. In this method, a sample is made to flow into the capillary column and a liquid phase in the column is allowed to retain the analyte, then the solvent is made to flow therethrough for desorbing the analyte by the use of the solvent. On the other hand, another method has been suggested in which a syringe is used and an analyte is retained by a hollow needle having a stationary phase being fixed on an inner surface of the hollow needle, then the analyte is desorbed by making a solvent flow through the needle or by heating the needle (Japanese Patent Laid-Open No. 8-94597). Conventionally, when the analyte is concentrated, a column whose cylindrical body is packed with a bead-like inorganic filler has been generally used.

In the former technique, a sample retention capacity is generally increased by making a thickness of the fiber liquid layer larger, in order to increase a sample capacity. However, there is a problem that the time required for equilibrating the analyte with the liquid phase becomes longer as the film thickness is increased. As for extraction of an agricultural chemical dissolved in water which is performed by actually using a liquid phase having a thickness of 100 μm, it has been frequently reported that the time required for reaching an equilibrium was 15 to 60 minutes or more (J. Beltram, F. J. L pez. F. Hern ndez Journal of Chromatography A. 885 (2000) 389-404). Although the equilibration time has been reduced by stirring the sample and by shaking the syringe or heating the sample for example in order to reduce the equilibration time, substantial reduction in the equilibration time has not been achieved (Makoto Okawa, Takashi Kasamatsu, Yoshiya Akiba, the 8$^{th}$ Symposium on Environmental Chemistry, Kyushu, 1999). In addition, this method cannot be applied to an analysis of a thermally decomposable component because the sample is thermally desorbed when the sample is introduced into the analytical system. When the thermal desorption in the SPME is performed at an injection port of an existing gas chromatograph, a peak width is finally broadened because a low boiling component largely diffuses at a time of its injection.

In the In-tube SPME method using a capillary column as well as in the In-tube SPME method using a syringe, a stationary phase is provided on an inner surface of the hollow needle and a center thereof is hollow. The sample freely passes through the hollow portion, thus, opportunities that the analyte diffuses into the stationary phase are reduced, and the time required for reaching an equilibrium becomes longer. In addition, it becomes necessary to increase an inner diameter of the needle and to increase the film thickness, in order to increase a sample capacity. However, as the inner diameter increases, a contact efficiency is reduced due to an extended diffusion time. Further, in a method which uses a column being packed with a filler, there are some problems as follows: (1) a flow rate depends on the packing state, so that analytical values will vary; and (2) resistance to a stream of the fluid becomes larger and the flow rate per unit time is decreased, so that the analytical time becomes longer. In this method, thermal desorption is also carried out at an existing GC injection port, so that broadening of a peak width cannot be avoided.

Therefore, an object of the present invention is: to increase a sample capacity relative to that obtained by the conventional capillary column; to reduce a distribution resistance relative to that obtained by a column packed with particulate substances; and to reduce a time required for reaching a distribution equilibrium of an analyte compared with that obtained by the conventional SPME or In-tube method, by the use of a porous body having an integral structure of open cell structures (a so-called monolithic structure) when a pre-treatment for introducing a sample into a chromatograph is performed. The present invention is widely applicable to pre-treatments of a gas chromatography, a high-performance liquid chromatography, and other analytical methods.

DISCLOSURE OF THE INVENTION

According to the present invention, a flow rate can be increased under a low pressure condition by improving a particle-packed type of column which has been commonly used and which requires a high pressure for passing a liquid (or a gas) through the column, and a time required for running one analysis can be reduced by improving the SPME pre-treatment which requires one hour or more for reaching an equilibrium state in the case of certain samples and then a great deal of time is required for running one analysis. Therefore, the first aspect of the present invention, which is a method for performing a solid-phase extraction of a component present in a sample and which utilizes a syringe having a cylinder and a plunger slidable within the cylinder, a tip of the syringe being provided with a needle and the needle being provided with a porous body having an integral structure of open cell structures (hereinafter, referred to as a so-called monolithic structure) along at least an appropriate length of the needle and across an overall diameter of the needle, is characterized by comprising the steps of inserting the needle into the sample, passing the sample through the needle to retaining an analyte within the porous body, and desorbing the retained analyte from the porous body.

The second aspect of the present invention is an apparatus for performing a solid-phase extraction of a component present in a sample, characterized in that the apparatus is constructed by a syringe having a cylinder and a plunger slidable within the cylinder, a tip of the syringe being provided with a needle and the needle being provided with a porous body having a so-called monolithic structure along at least an appropriate length of the needle and across an overall diameter of the needle, such that the sample is retained within the porous body when the sample passes through the needle and the sample can be desorbed from the porous body.

The third aspect of the present invention is a method for performing a solid-phase extraction of a component present in a sample, characterized in that a syringe has a cylinder and a plunger slidable within the cylinder, a tip of the syringe being provided with a needle and the needle being provided with a porous body having a so-called monolithic structure along at least an appropriate length of the needle and across an overall diameter of the needle, and that the entire needle or at least a portion of the needle within which the porous body is formed is attachably and detachably provided for the syringe or the needle with an analyte retained within the porous body by passing the sample through the porous body when the sample passes through the needle.

The fourth aspect of the present invention is an apparatus for performing a solid-phase extraction of a component present in a sample, characterized in that a syringe has a cylinder and a plunger slidable within the cylinder, a tip of the syringe being provided with a needle and the needle being provided with a porous body having a so-called monolithic structure along at least an appropriate length of the needle and across an overall diameter of the needle, and that the entire needle or at least a portion of the needle within which the porous body is formed is attachably and detachably provided for the syringe or the needle.

The fifth aspect of the present invention is a needle attachably/detachably formed at a needle securing part provided for a tip of a syringe or for a syringe, characterized in that the needle is provided with a porous body having a so-called monolithic structure across at least an overall diameter of an inner diameter along an appropriate length of the needle.

In the sixth aspect of the present invention, the needle described in the above fifth aspect is characterized in that the needle is a sample tip.

In the seventh aspect of the present invention, the needle described in the above fifth aspect is characterized in that the needle is provided with an outer cylinder outside the needle.

In the eighth aspect of the present invention, the method for performing a solid-phase-micro extraction described in the above first or third aspect is characterized in that the porous body is a single pore.

In the ninth aspect of the present invention, the apparatus for performing a solid-phase-micro extraction described in the above second or fourth aspect is characterized in that the porous body is a single pore.

In the tenth aspect of the present invention, the method for performing a solid-phase-micro extraction described in the above first or third aspect is characterized in that the porous body is a double pore.

In the eleventh aspect of the present invention, the apparatus for performing a solid-phase-micro extraction described in the above second or fourth aspect is characterized in that the porous body is a double pore.

BEST MODE FOR CARRYING OUT THE INVENTION

The present invention is a method in which a needle provided with a porous body having a so-called monolithic structure across an overall diameter of the needle is used for retaining a gas, liquid, or solid sample including an analyte by the porous body and for concentrating the sample, while passing the sample through the needle. Then, the sample is desorbed by making a certain kind of solvent flow into the needle or the sample is physically desorbed by heating the needle for example after the concentration, and the desorbed sample is introduced to an analytical system such as a gas chromatograph.

A syringe is comprised of a cylinder, a plunger slidably provided within the cylinder, and a needle provided at a tip of the syringe. A porous body is formed along an appropriate length of the needle and across an overall diameter of an inner diameter of the needle. The length and the pore size can be selected based on a material of the porous body, a pore to be provided, an analyte or the like.

When a column is packed with a non-porous filler, pores are provided only between particles, and such structure is referred to as a single pore. When a column is packed with silica gel particles having pores, a pore is provided within a particle and also pores are provided between particles, so that a double structure is formed. This is referred to as a double pore. Although the single pore is formed when a column is packed with a non-porous filler, a shape of the space will vary depending on a filling state of the particles, so that a separation mode becomes complicated. On the other hand, separation by the double pore does not result in a simple adsorption distribution, so that the separation mode is not simple. Therefore, a single pore in which the shapes of spaces do not vary is recommended. This can also be said in the case of the porous body.

The utility of the porous body having a so-called monolithic structure will be described.

A solid-phase extraction, in which a solid phase is provided on a surface of a fiber or a needle, has various problems such as that described in Problems to be Solved by the Invention. A simple method for solving the problems is to fill particles acting as a homogeneous solid phase with in a needle. Generally, when a column or the like is packed with particles, an inter-particle space where a mobile phase is flow through a gap between particles is created.

The spaces are determined by the filling state of the particles, so that the spaces do not necessarily become uniform. Further, the spaces may vary under the influence of the mobile phase and lack in their reproducibility. In order to avoid the influence of the spatial ununiformity, a high-performance liquid chromatography in which a mobile phase is delivered at a high pressure is designed to improve its spatial uniformity by making particles to be packed smaller and by making a space through which the mobile phase flows smaller.

However, as the particle size becomes smaller, the resistance at a time when the mobile phase such as gas or liquid flows is decreased, so that the problem in which the mobile phase can not be made to flow smoothly comes up. Therefore, in the solid-phase extraction which is not available at a high pressure, particle sizes of the particles to be packed must be larger. However, when the particles are larger, the inter-particle spaces become ununiform and the control also becomes difficult, so that the initial problem in which a solid-phase extraction having a good reproducibility is not achieved cannot be solved. In addition, the larger particle size makes the inter-particle space larger, so that the time difference is produced when molecules are distributed to surfaces of the particles. This results in broadening of a sample band, that is, a decrease in separation efficiency.

In view of the above-described facts, a porous body having a so-called monolithic structure where a space through which a mobile phase flows can be uniform has become of interest. In this structure, the space through which the mobile phase flows means a pore of the porous body. The superiority of this monolithic structure has already been summarized in literatures or the like (Analytical Chemistry vol. 73 No. 5421A-429A (2000)).

Particularly, in a micro solid-phase extraction where a small volume of sample is used, small pores other than spaces through which a mobile phase flows do not significantly affect the separation, so that a single pore type of porous body which has only mobile phase spaces is sufficient for the separation. In the so-called monolithic structure of the single pore type, ununiformity will not occur in the space, so that the separation by adsorption and elution is performed smoothly. In the separation of a macromolecule, if additional pores into which molecules can be incorporated and whose sizes are different from the spaces through which the mobile phase flows exist, desorption can not be smoothly performed and this may be sometimes inconvenient.

Therefore, the single pore type structure is useful for a micro solid-phase extraction of a macromolecule including proteins. This is a reason why the above-described single pore is recommended.

On the other hand, if an amount of a matrix including an analyte is increased, a surface is covered with the matrix, so that the separation of the analyte sometimes cannot be performed. To decrease an influence of the matrix, it is useful to increase a surface area. There are two methods for increasing the surface area: one is to form particles or the like on a surface of a pore (through pore) structure through which a mobile phase flows by performing another post-treatment; and the other is to simultaneously form a pore through which a mobile phase flows (a through pore) and a pore whose diameter is smaller than that of the above described through pore (a meso pore) in a skeletal structure.

The so-called monolithic structure formed by the latter method can be referred to as a double pore structure which has a through pore structure communicating from an upper end to a lower end and has a meso pore in a skeleton formed in the communicating pore. The meso pore is essential for retaining and separating a compound with a high degree of efficiency, so that the pore size may be within a certain range such that a molecule intended to be separated can be passed through the pore and it is appropriate that the pore size is within a range from 5 nm to 100 μm.

In the former method, it is possible to form a particle whose property is different from a so-called monolithic structure which becomes a skeleton, so that it also becomes easy to reduce its adsorptivity. In addition, a particle to be formed can be freely selected, and a non-porous particle or the like which does not affect proteins can also be formed. An arbitrary porous body can be formed based on its intended use.

On the other hand, in the latter method, an internal particle cannot be formed arbitrarily as in the case of the former method and the composition becomes constant, but the surface area can be increased by providing pores having different sizes by carrying out a synthesizing treatment once. This method is very useful for production, and in addition, chemical binding groups can be uniformly introduced since a uniform composition can be formed, so that this method is effective for extracting a solid-phase which contains a wide variety of low-molecular weight compounds having various properties. This is a reason why the double pore is recommended as described above.

Whether the single pore is optimum or the double pore is optimum is determined depending on a sample, a property of an analyte, and a purpose of the pre-treatment. In either case, it is important that the porous body having a so-called monolithic structure which has uniform pores through which a mobile phase smoothly flows becomes a solid phase.

Then the Porous Body Will be Described

The porous body used in the present invention has a pore described below and the pore has a structure communicating from an upper end to a lower end, that is, a so-called monolithic structure. In addition, it is preferable that an axial section of the pore is circular or almost circular, and although a material of the porous body is not particularly limited as long as a macro pore size can be controlled within a range described below, the material is an inorganic porous body such as a porous ceramic or a porous glass and for example the porous glass is desirable. Among examples of the porous glass is a glass having an NaO—$B_2O_3$—$SiO_2$—CaO based composition, and the porous glass may be manufactured by using a glass to which various oxides such as $Al_2O_3$, $ZrO_2$, $ZnO_2$, $TiO_2$, $SnO_2$ and $MgO_2$ are added.

A method for fabricating the porous glass has been suggested in which a borosilicate glass is subjected to a heat treatment to form an entanglement separation phase structure utilizing a separation phase phenomenon, before eluting acids from either of these phases. For example, silica sand, boric acid, soda ash and alumina are mixed together and fused at 1200 to 1400° C. After the fused mixture is molded at 800 to 1100° C., a borosilicate glass whose phase has not been yet divided is obtained, and this glass is subjected to a heat treatment to be divided into a $SiO_2$ phase and a $B_2O_3$—$Na_2O$—CaO phase and then subjected to an acid treatment to manufacture a porous body preserving a $SiO_2$ skeleton therein. A pore size can be controlled by changing the conditions of carrying out the heat treatment based on the intended use and the diameter can be within a range of 0.1 to 10 microns having a uniform distribution of pores.

Among examples of the porous ceramic are silica, alumina silicate A (obtained by sintering hard magnetic particles), silica sand, alumina, alumina seriate B (obtained by sintering chamotte particles), porous mullite, diatomaceous earth and the like. The porous ceramic is manufactured, for example, by mixing ceramic particles whose particle sizes are within a certain range (such as hard magnetic ground products, silica, alumina, and chamotte) and pore forming materials such as crystalline cellulose (Asahi Kasei: Abicell) with an appropriate dispersion solvent and then molding and sintering the obtained mixture. The porous ceramic, whose pore size is within or beyond a range from about 500 μm to about 0.1 μm and whose pore distribution is uniform, can be manufactured depending on its usage.

The above-described pore is obtained by modifying an inner surface of a pore by using a coating agent and/or a chemical modifier suitable for a separation sample used for a conventional filler. Among the coating agents are polyethylene glycol and silicone oil for example. And among the chemical modifiers are various kinds of silane finishing agents such as: alkylchlorosilanes including trimethylchlorosilane (TMS), dimethyl-n-octylchlorosilane, and dimethyl-n-octadecylchlorosilane (ODS); aminoalkoxysilanes including r-aminopropyltriethoxysilane; and other epoxysilanes. In addition, high molecular compound such as proteins or low molecular compounds may be bonded to modified groups of a surface modifier.

In addition to the above-described porous body, it is recommended to use a porous body whose structure is made by filling the pores of above described porous body with porous bodies having micropores. This porous body will now be described.

Macropores of a skeletal body having macropores is impregnated with monomers for forming micro porous bodies, and the monomers are polymerized within the macropores by the use of a solvent or the like which has already been added to the monomers, then the macropores are filled with porous bodies which are smaller than the macropores and which have open structures and micropores, so that a porous body having an integral structure is produced. In this case, the monomer for forming the micro porous body may be either of organic materials and inorganic materials, and if the monomer is inorganic, a porous silica glass having micropores can be formed as follows. That is, a catalyst such as hydrochloric acid is added to tetraethoxysilane to prepare a sol, and the macropores are impregnated with the sol before aging. On the other hand, if the monomer is organic, various kinds of resins can be selected. For example, a polyacrylamido gel porous body can be obtained by initiating polymerization after the macropores are impregnated with acrylamido monomers. A range of the micropore is determined based on a particle size of an analyte to be separated which is present in a liquid. Even a chemical compound which has a higher-order structure in a liquid, as in the case of proteins, can be sufficiently incorporated within a pore as long as the size of the chemical compound is up to 1000 nm due to a liquid affinity. Preferably, the size is 100 to 500 nm.

In addition, a method for forming an inorganic porous body by a sol-gel process utilizing a liquid phase reaction is also known. The sol-gel process is a method for producing the so-called polymerizable low molecular compounds to finally obtain aggregates and polymers, thus the following procedures are performed. Specifically, water soluble macromolecules and a nonionic surfactant are dissolved in an acidic aqueous solution, to which metallic compounds having hydrolyzable functional groups are added for inducing a hydrolytic reaction, then after the products are solidified, dry-heating or solvent substitution is performed. This method utilizes a phenomenon in which phase separation of the uniformly dispersed water soluble macromolecules or nonionic surfactant occurs in the course of hydrolyzation and polymerization of metal alkoxides or oligomers thereof.

A nonionic surfactant and heat decomposable compounds are dissolved in an acidic aqueous solution, to which metallic compounds having hydrolyzable functional groups are added for inducing a hydrolytic reaction, then after the products are solidified, a gel in a wet condition is heated to pyrolyze low molecular compounds which have already been dissolved therein at the time of preparing the gel, then dried and heated.

In this case, the metal alkoxides or oligomers thereof are preferably compounds having functional groups with less carbon atoms such as a methoxy group, an ethoxy group, and a propoxy group. In addition, as a metal present in the compound, a metal present in an oxide to be finally produced such as Si, Ti, Zr, or Al is used. This compound may include one or more metals. In particular, silicon alkoxide is preferable, and tetramethoxysilane, tetraethoxysilane, methyltrimethoxysilane, ethyltrimethoxysilane, or vinyltrimethoxysilane can be used as the silicon alkoxide, but the silicon alkoxide is not limited to the above-described compounds. On the other hand, the oligomers which can uniformly dissolved and dispersed in alcohol may be used, and specifically, about up to a decamer can be used. Organic macromolecules are preferably mixed with the metal alkoxides or oligomers thereof in the proportion of 0.03 to 0.40 part by weight to 1 part by weight.

The water soluble organic macromolecules, which provide the phase separation in the course of hydrolization and uniformly dissolve in an alcohol containing liquid produced by hydrolyzation of alkoxides or oligomers thereof produced by hydrolyzation of the metal alkoxides or oligomers thereof, may be used. Specifically, polymeric metallic salts such as a sodium salt of polystyrenesulfonic acid, polymeric acids such as polyacrylic acid which becomes a polyanion by dissociation, polymeric bases such as polyallylamine and polyethyleneimine which produce polycations within an aqueous solution, or neutral polymers such as polyvinylpyrrolidone having v-lactam at a side chain of polyethyleneoxide or the like having ether bonds at a main chain are preferably used.

The nonionic surfactant is a substance which induces sol-gel transformation and phase separation processes simultaneously, thus the original phase is separated into a solvent rich phase and a skeletal phase, and simultaneously, these phases are gelatinized. As the nonionic surfactant, it is preferable to use a compound including a hydrophilic portion such as polyoxyethylene and a hydrophobic portion mainly comprised of an alkyl group, that is, polyoxyethylenenonylphenylether, polyoxyethyleneoctylphenylether, and polyoxyethylenealkylether for example. And as the hydrophilic portion, it is preferable to use an entity including polyoxypropylene, that is, polyoxypripylenealkylether for example. However, the nonionic surfactant is not limited to the above-described substances. Although an amount of the nonionic surfactant to be added depends on a kind of the surfactant, a kind of the metal alkoxide and an amount thereof, the amount of the nonionic surfactant is 1.0 to 10.0 g and is preferably 1.5 to 6.0 g relative to 10 g of the metal alkoxide.

When a nonionic surfactant and heat decomposable compounds are dissolved in an acidic aqueous solution to which metallic compounds having hydrolyzable functional groups are added for inducing a hydrolytic reaction, then a gel whose phase is separated into a solvent rich phase and a skeletal phase is produced. After the products (gel) are solidified, and after a lapse of an appropriate aging time, the gel in a wet condition is heated to pyrolyze the heat decomposable compounds which have already been dissolved in a reaction solution, then a pH value of the solvent which is in contact with an inner wall of the skeletal phase is increased. Then, the solvent erodes the inner wall and modifies an unevenness of the inner wall to gradually increase the pore size.

In general, mineral acid such as hydrochloric acid or nitric acid whose normality is 0.001 or more is preferably used as an acidic aqueous solution to be used in this case. The hydrolysis is achieved by placing such solution in a closed vessel and retaining the solution within the vessel for 0.5 to 5 hours in an atmosphere whose temperature is 40 to 80° C. In this hydrolysis, a solution which was initially clear becomes whitish and organic macromolecules undergo phase separation, then the phases are gelatinized. The organic macromolecules or polymers thereof in this hydrolyzing process is in a dispersing state, so that the organic macromolecules or polymers thereof are not substantially precipitated.

Thus gelatinized substances are allowed to stand for about several hours to several tens of hours at 40 to 80° C. for their aging, then the gel is washed with water to remove the organic macromolecules and sintered at 800 to 1,000° C. to obtain a porous glass.

The porous column having the so-called monolithic structure has become a very rigid structure in terms of an entire skeletal body, by fixing a brittle porous body glass or porous ceramic obtained through the sol-gel process within macropores of a porous body glass or porous ceramic which is a rigid skeletal body. Therefore, a sealing of its periphery can be easily achieved by hermetically placing a ring, such as Teflon or polypropylene which has been conventionally used for a filter or the like, around the periphery.

Example 1

Figure 1:
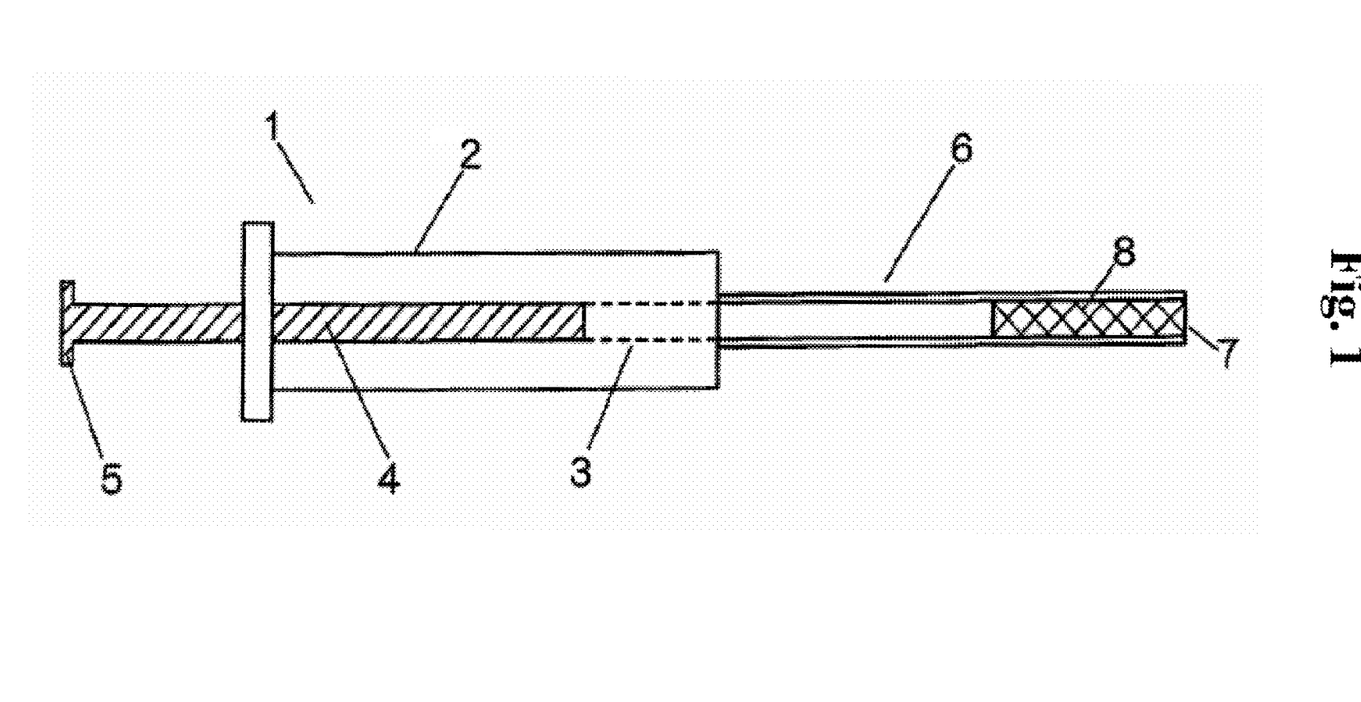
FIG. 1 is a side view illustrating a syringe used for the present invention, which is partially sectioned in a vertical direction.

An example of the present invention will be described with reference to FIG. 1.

A syringe 1 is comprised of a cylinder 2 and a plunger 4 which is slidably provided within an inner cylinder 3 of the cylinder 2. A head portion of the plunger 4 is provided with a handle 5. A tip of the cylinder 2 is provided with a needle 6. An inside of the needle 6, over a length of 4 mm thereof, is packed with a cylindrical porous body 7 which is made of a porous glass and through which pores 8, 8, . . . are formed along an axial direction, the average pore size being 10 μm.

A procedure for manually actuating the syringe 1 will be described with reference to FIG. 2. Methanol or the like is firstly passed through the needle 6 for conditioning a state of the porous body. The needle 6 is inserted through a sample bottle 9, then the sample is sucked up by actuating the plunger 4, FIG. 2(a). This suction allows the sample to pass through the porous glass of the porous body 7 when the sample passes through the needle 6. At this time, the analyte is diffused and retained in the pores 8, 8, . . . . A predetermined amount of sample can be sucked at one time or can be sucked by pumping operation as required. In addition, the sampling can be performed by removing the needle 6 from the sample bottle 9 at every single suction, and pushing down the needle 6 to ejecting the sample other than the analyte, and then inserting the needle 6 through the sample bottle 9 again to repeating the same operation as described above. Further, the sample solvent can also be ejected from the needle 6 by making a wash gas or the like to flow through the needle 6.

Figure 2:
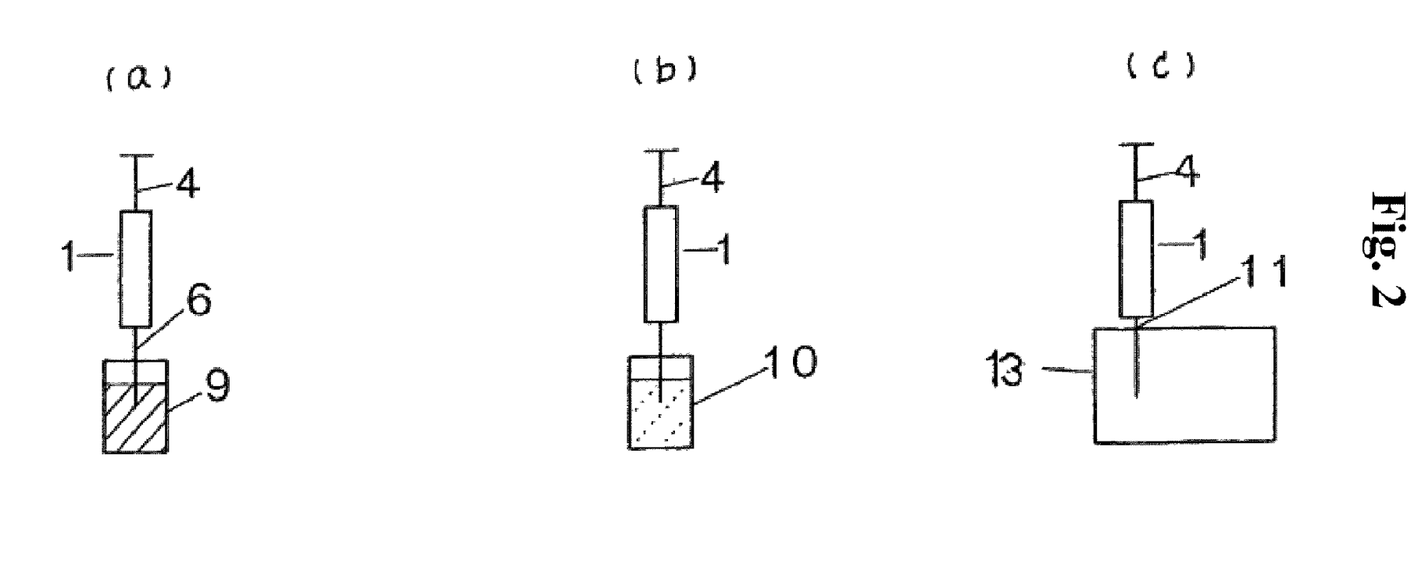
FIG. 2 illustrates the practice of a method according to the present invention.

Then, the needle 6 is removed from the sample bottle 9 and inserted into a solvent bottle 10 to perform suction of the solvent, FIG. 2(b). According to this solvent suction, the analyte is desorbed from the pores 8, 8, . . . and kept within the cylinder 2 of the syringe 1 or within the needle 6. Then, the syringe 1 is set on a gas chromatograph 13, and the solvent into which the analyte is extracted is injected into the gas chromatograph 13 via a fill port 11 by pushing down the plunger 4 in order to perform its analysis, FIG. 2(c).

Example 2

A next example of the present invention will be described with reference to FIG. 3.

In contrast to Example 1 in which the analyte is eluted by the solvent, this example uses heat instead of the solvent in order to desorb the sample.

Figure 3:
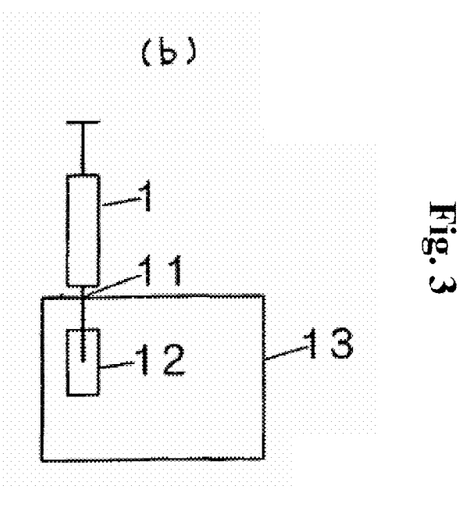
FIG. 3 illustrates the practice of other method according to the present invention.

Specifically, the sample is sucked by actuating the plunger as in the case of Example 1, FIG. 3(a). Then, a heating mechanism 12 which is ordinary provided at the injection port 11 of the gas chromatograph is utilized. The needle 6 containing the sample which is diffused and retained in the pores 8, 8, . . . of the porous body as in the case of the above-described Example 1 is inserted into the injection port 11. Gas is supplied from a supplying port which is provided at an upper portion or a middle portion of the syringe 1 and the needle 6 is heated by the heating mechanism 12, then the sample undergoes physical desorption and is introduced into the gas chromatograph, FIG. 3(b).

Example 3

Figure 4:
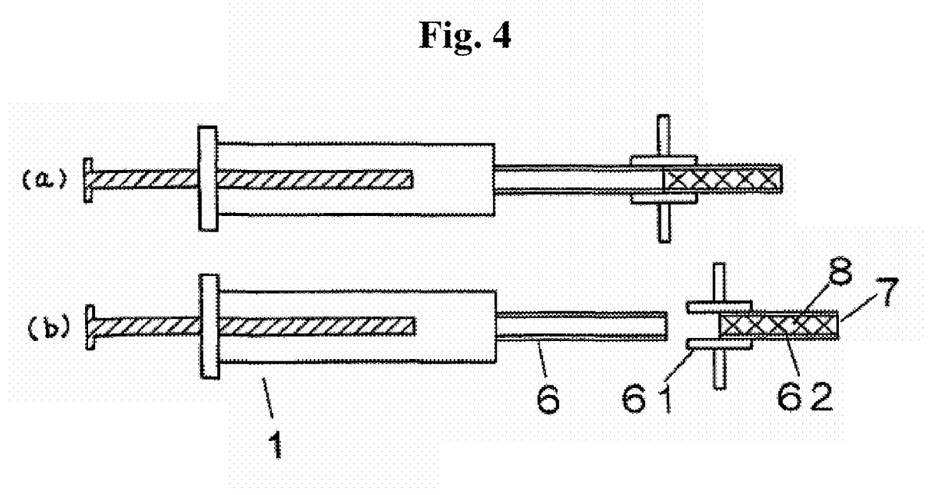
FIG. 4 illustrates the practice of other syringe used for the present invention.
Figure 5:
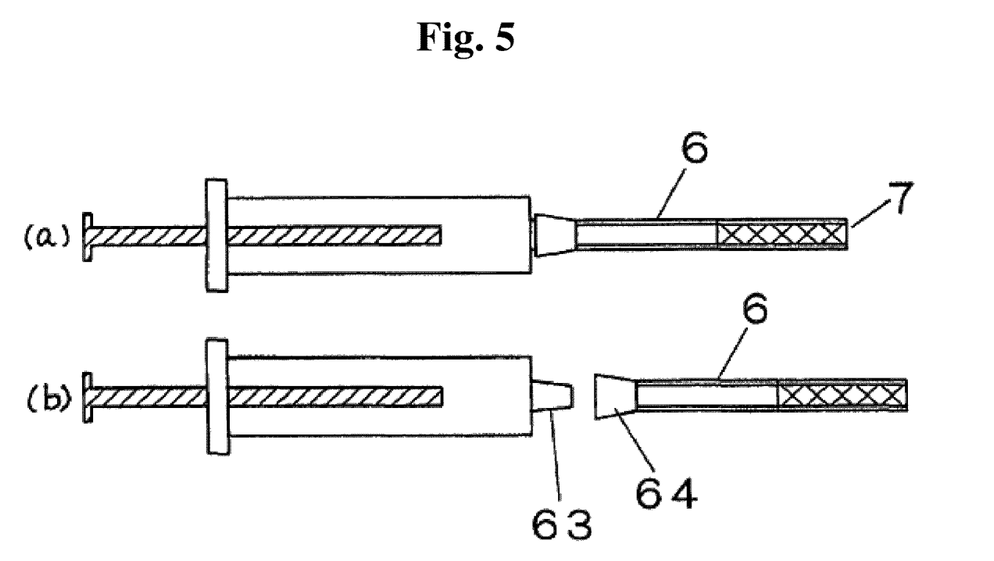
FIG. 5 illustrates the practice of other syringe used for the present invention.

Another example of the present invention will be described with reference to FIG. 4 and FIG. 5.

In this example, the needle 6 is constructed to be attachable/detachable with respect to the syringe 1. In this construction, the needle 6 is made short, and the tip of the needle 6 is provided with a capillary 62 having an insertion part 61 for the needle 6. This capillary 62 is constructed to be attachable/detachable with respect to the needle 6 with the above described cylindrical porous body 7 formed within the capillary 62 (FIG. 4). In this case, a tapered sample tip which has been conventionally used for chemical reactions or immunoreactions can be used as the capillary 62 with the porous body formed therein. In addition, as another example, a holding part 63 for holding the needle 6 is formed at a tip of the syringe 1 and also the corresponding insertion part 64 is provided at the needle 6 (FIG. 5).

Further, it is of course possible to use a tapered sample tip 65 having an insertion part for the syringe cylinder as the entire needle 6 and to insert the tapered sample tip 65 into the holding part 63.

Figure 6:
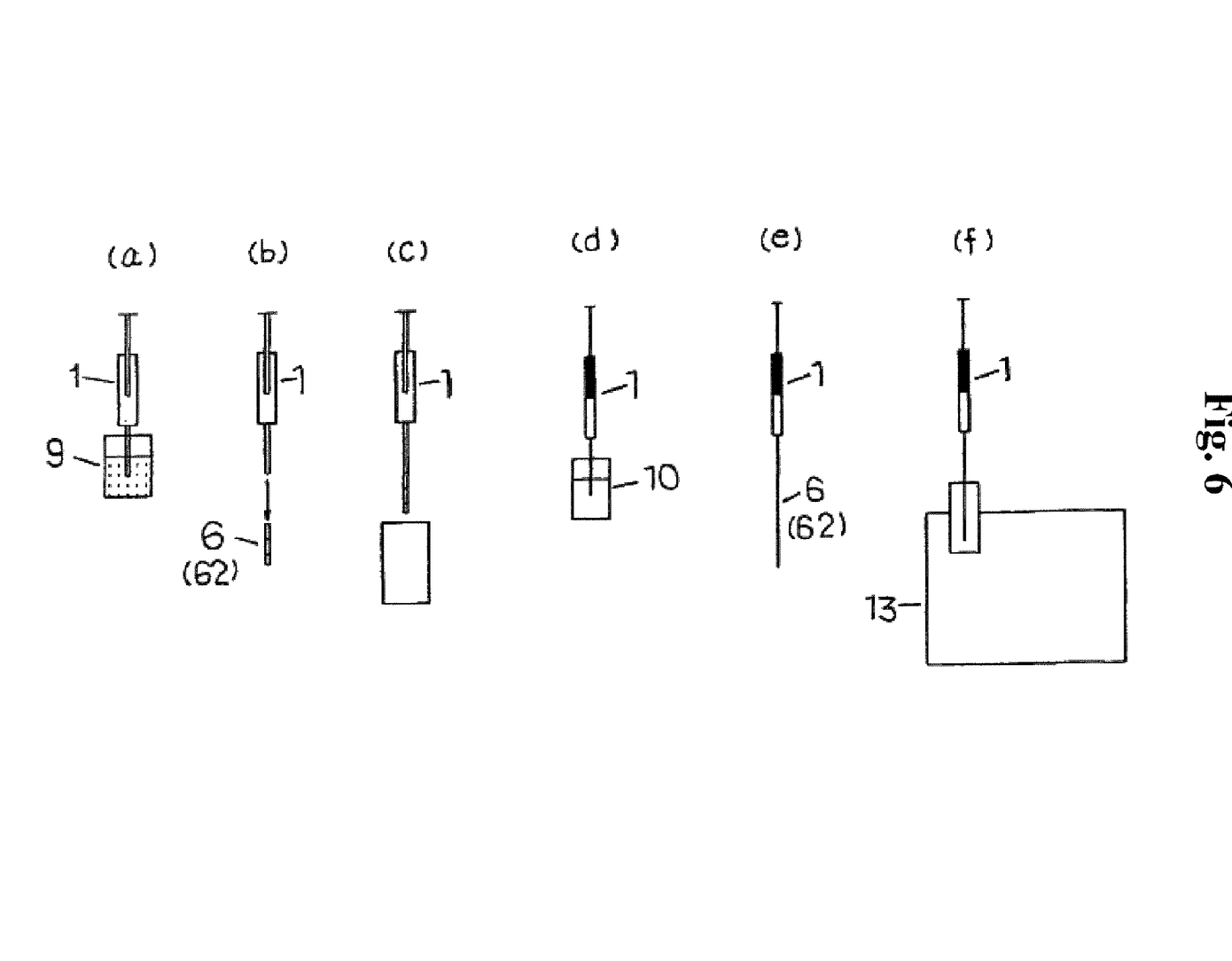
FIG. 6 illustrates the practice of other method according to the present invention.

An example of the operation will be described with respect to FIG. 6. First, a 250 μl of syringe 1 with the needle 6 or the capillary 62 removed therefrom is used to suck up a water sample to which an agricultural chemical is added, FIG. 6(a). Then, the needle 6 or the capillary 62 (herein after, the same as above), within which a porous body chemically modified by $C_{18}$ having an inner diameter of 200 μm and a length of 50 mm is formed, is attached to the syringe 1, FIG. 6(b). The plunger 4 is pushed down to pass the sample through the needle 6 so that the analyte is retained in the pores 8, 8, . . . , FIG. 6(c). After all of the sample is ejected, sucking operation of the syringe 1 is carried out to remove water remaining in the porous body 7. Then the needle 6 is removed from the syringe 1. Then, another 100 μl syringe 1 is used to meter 20 μl of solvent which includes hexane and ethyl acetate in proportions of 3:1, FIG. 6(d). The above-described needle 6 retaining the analyte is attached to the 100 μl syringe 1, FIG. 6(e). The needle 6 is inserted into the injection port of the chromatograph. The plunger 4 is pushed down to elute the analyte by the solvent, and the agricultural chemical is introduced to the chromatograph 13, FIG. 6(f). The analytical condition of chromatography is as follows.

Injection port temperature: 40° C. to 250° C., a temperature rising rate is 1° C. per second (on-column injection).

GC temperature: 40° C. (one minute) to 250° C. (5 minutes), a temperature rising rate is 15° C. per minute.

Column: a capillary column where dimethylpolysiloxane is chemically modified, inner diameter 0.25 mm, length 15 m, film thickness 0.25 mm.

Detector: FPD 200° C.

Solid-phase porous body column for extraction: inner diameter 0.2 mm, length 50 mm.

Figure 7:
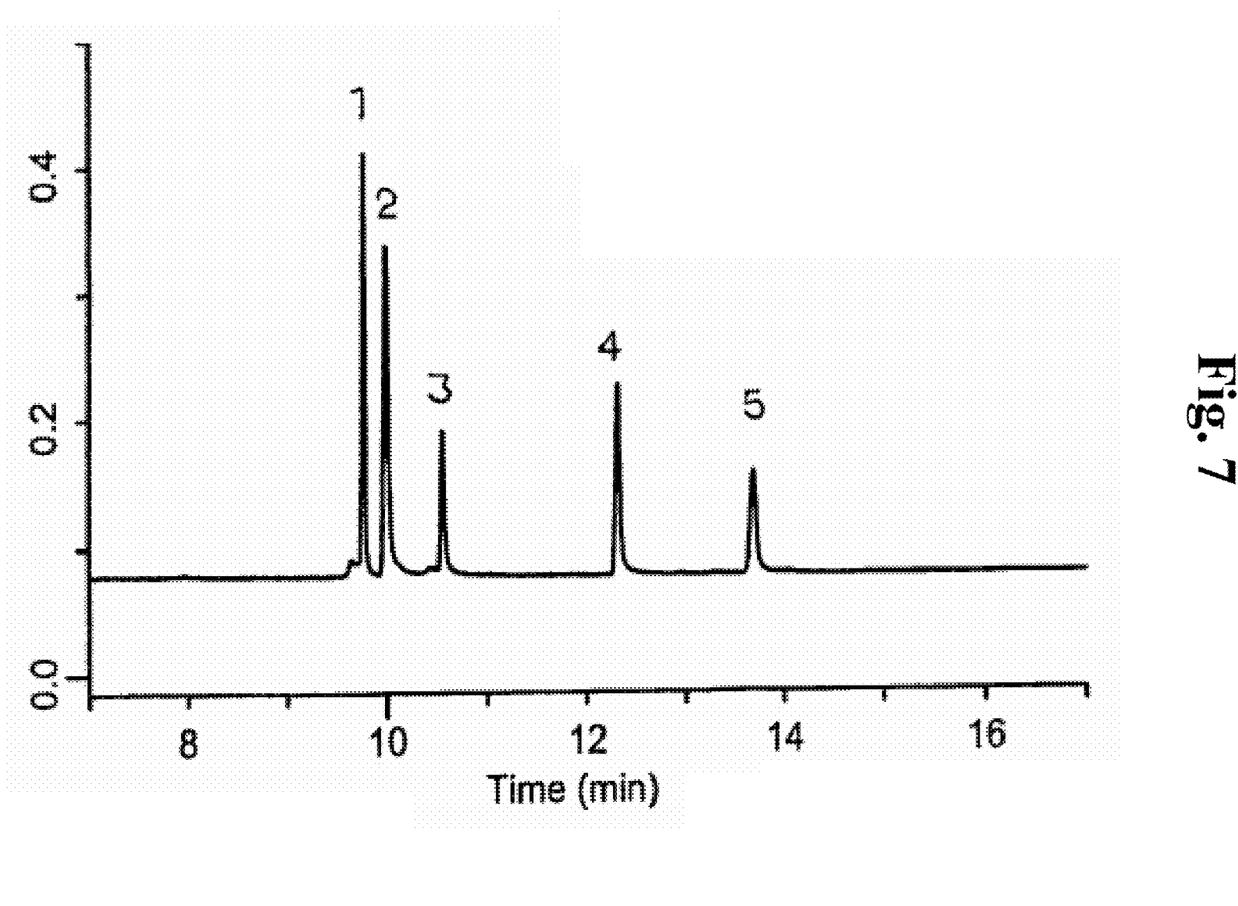
FIG. 7 is a chromatogram obtained by an experimental example carried out according to the present invention.
Figure 8:
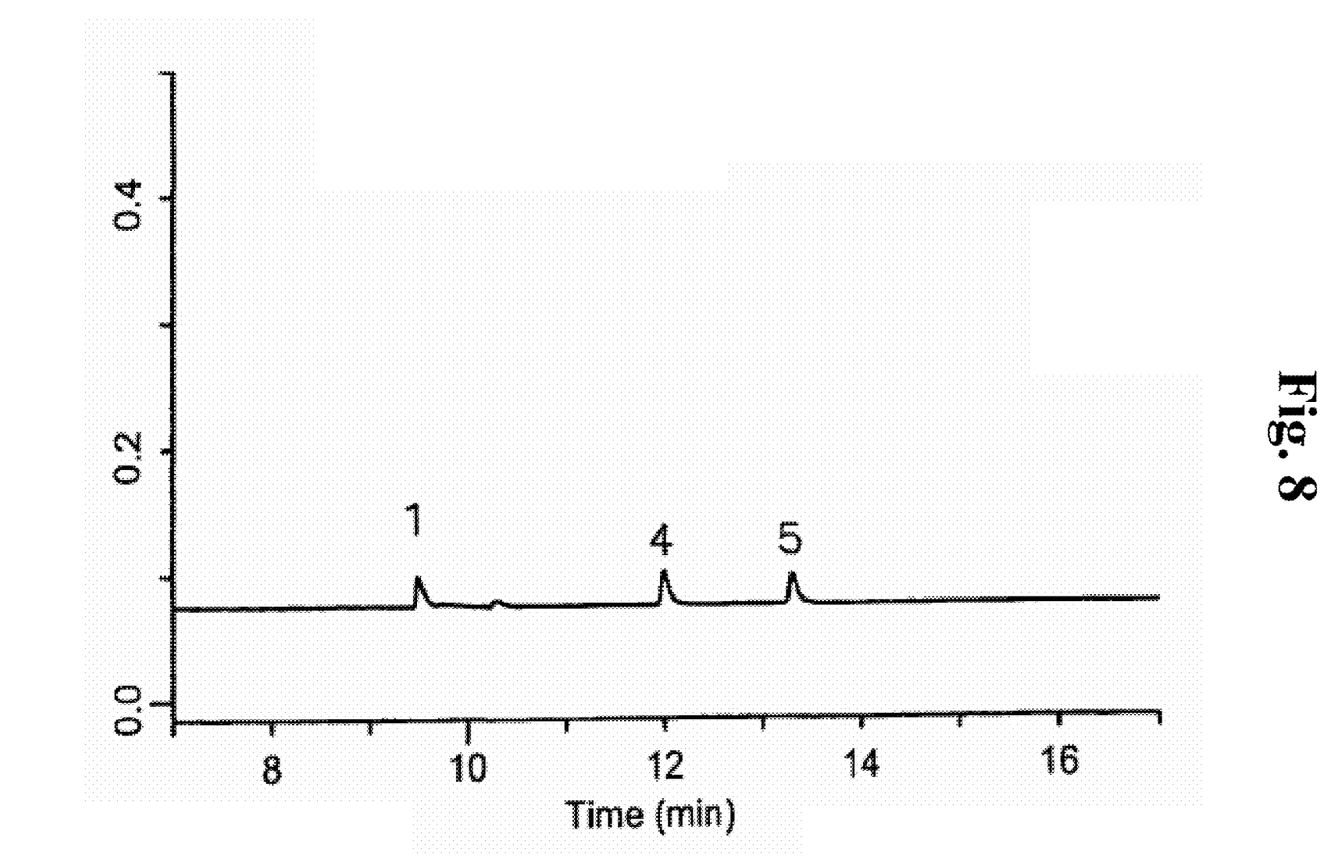
FIG. 8 is a chromatogram obtained by the above described experimental example which has been carried out by means of a hollow column.

A chromatogram obtained as a result of this sample analysis is shown in FIG. 7. In this figure, a peak 1 represents Diazinon, a peak 2 represents Iprobenphos, a peak 3 represents fenitrothion, a peak 4 represents isoxathion, and a peak 5 represents EPN. On the other hand, FIG. 8 shows a chromatogram obtained by using an intube method, in which an inner surface of a capillary tube is chemically modified by 5% diphenyl 95% dimethylpolysiloxane, to extract the agricultural chemical dissolved in water by the same operation. The analytical condition is the same as that shown in FIG. 7. In the intube method, peak can hardly be recognized because the time required for reaching an equilibrium state becomes longer, but in the present method, it has been found that the extraction has completed within a short time and the analysis is possible.

Sampling by the gas chromatograph is generally automated by using an auto-sampler. When the syringe according to the present invention is applied to the auto-sampler, the time for extraction and desorption can be substantially reduced compared to the ordinary sold-phase extraction, so that the automation can be realized as in the case of a direct sampling of commonly used liquid or gas. Further, as for the current automatic analyzer for performing the solid-phase-micro extraction, only one extraction site can be provided for the syringe. Therefore, the extraction site becomes required to be manually replaced with new one if the extraction site deteriorates, or if a kind of chemically modified portion to be extracted and its thickness are intended to be changed. However, according to the present invention which allows for attachment/detachment of the needle of the syringe with the porous body formed therein, only the extraction site can be automatically replaced with new one, so that the automation becomes possible as a whole.

A pipette type of syringe will be described as one of the examples which utilize the syringe 1 for the pre-treatment.

A needle 6 with a cylindrical porous body 7 formed therein is connected to a tip of the cylinder 2 of the syringe 1. The detachable needle 6 described in this example is usually referred to as a sample tip 65. Referring to the sample tip 65 shown in FIG. 9, an open end 66 of the tapered needle 6 is freely inserted into and removed from the syringe 1, and the tip of the needle 6 or a part thereof is packed with the porous body 7.

Figure 9:
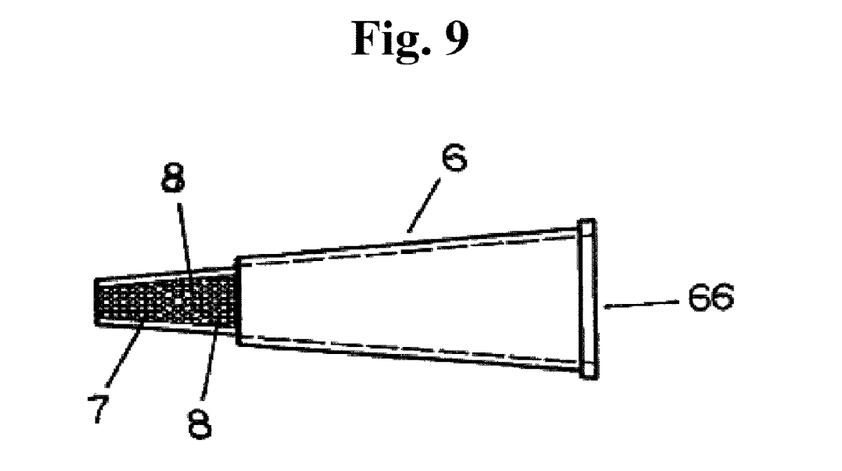
FIG. 9 is an explanation drawing of other example according to the present invention.

A handle 5 of the syringe 1 is manipulated to push down the plunger and the needle 6 is inserted into a micro-sample, then the pumping operation of the plunger is carried out to repeat the injection into and the ejection from the needle 6. After this operation, the sample is ejected from an ejection port of the needle 6 by the use of an appropriate mobile phase.

According to the simple operation, the analyte from the sample and occasionally impurities are adsorbed by and separated from the solid phase, and after the separation, the purification can be surely performed by selecting a mobile phase for elution as appropriate. In addition, only the sample tip 65 can be sequentially disposed since the needle 6 is a detachable sample tip 65, so that a plurality of samples can be subjected to the pre-treatment quickly and without being contaminated.

In a field of clinical diagnosis or gene diagnosis, or in a biochemical experiment, a large amount of liquid samples are required to be treated within a short time, so that a multi well plate in which a plurality of wells (pores) are provided has been generally used for the sampling. In addition, the above described detachable and disposable tip is used for sucking and discharging the sample which is stored in the wells. Such disposable tips have been frequently used recently because contamination between the samples and clinical infection can be prevented by using the disposable tips even when a micro-sample in the well described abode is analyzed and also a large amount of sample is analyzed.

Figure 10:
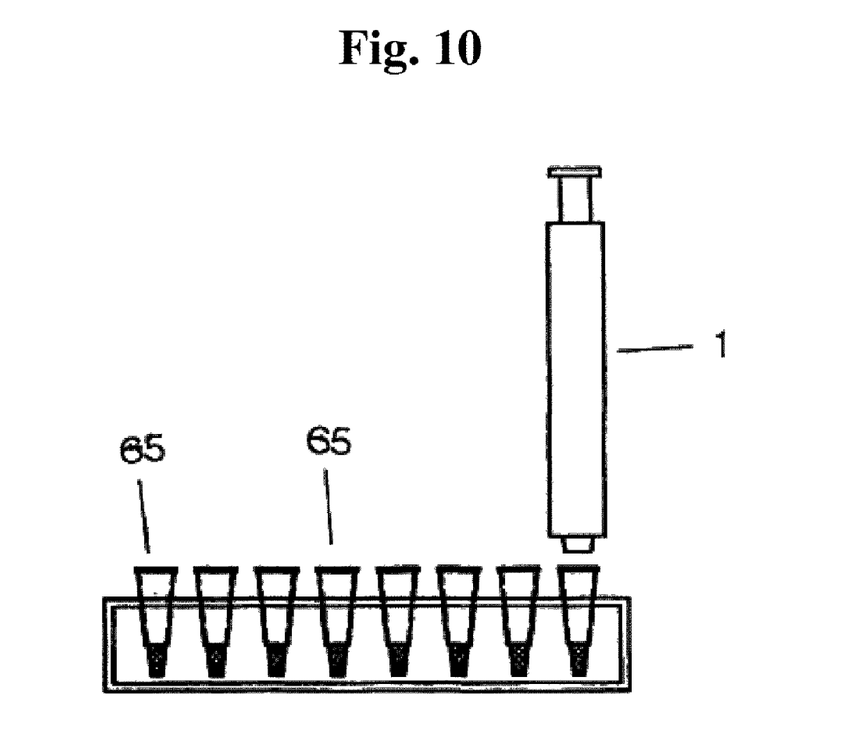
FIG. 10 illustrates the use of other example according to the present invention.

Further, the sample pre-treatment which is performed following the instructions from the automated treatment apparatus has been generalized. In this automated treatment apparatus, a pipette or a syringe body is provided with a nozzle for sampling. The nozzle moves along a lack in which the sample tips are placed and a sample tip to be used is selected, then the sample tip is attached to a tip of the nozzle (FIG. 10). Next, the nozzle moves on a sample well containing a liquid of interest, where a necessary pre-treatment such as sucking or discharging is carried out by actuating the pipette following the instructions from the automated treatment apparatus, then the sample tip after being subjected to the treatment is discarded. After this treatment, the same operations are repeated for each of the corresponding samples sequentially. Therefore, it becomes possible to treat a large amount of samples within a short time.

On the other hand, if a plurality of nozzle portions are previously provided for the pipette or syringe body, it is not necessary to move the nozzle sequentially on the sample tip of interest, so that it becomes possible to carry out the pre-treatment of all of the sample tips in a single operation. If a plurality of the nozzles whose number is the same as that of the sample wells are provided, a pre-treatment for all of the wells is completed in a single operation, so that an automated sampling can be achieved within a shorter time.

Figure 11:
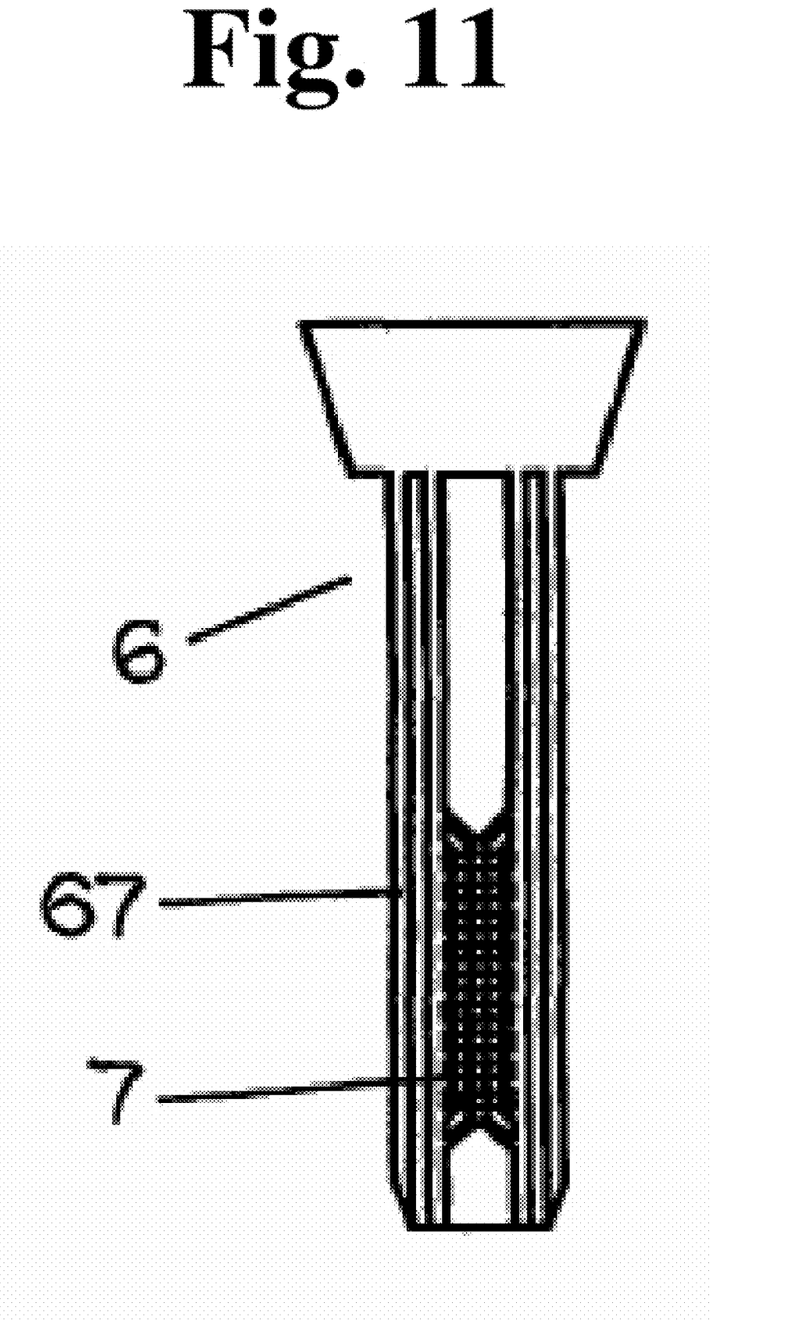
FIG. 11 is an explanation drawing of other example according to the present invention.
Figure 12:
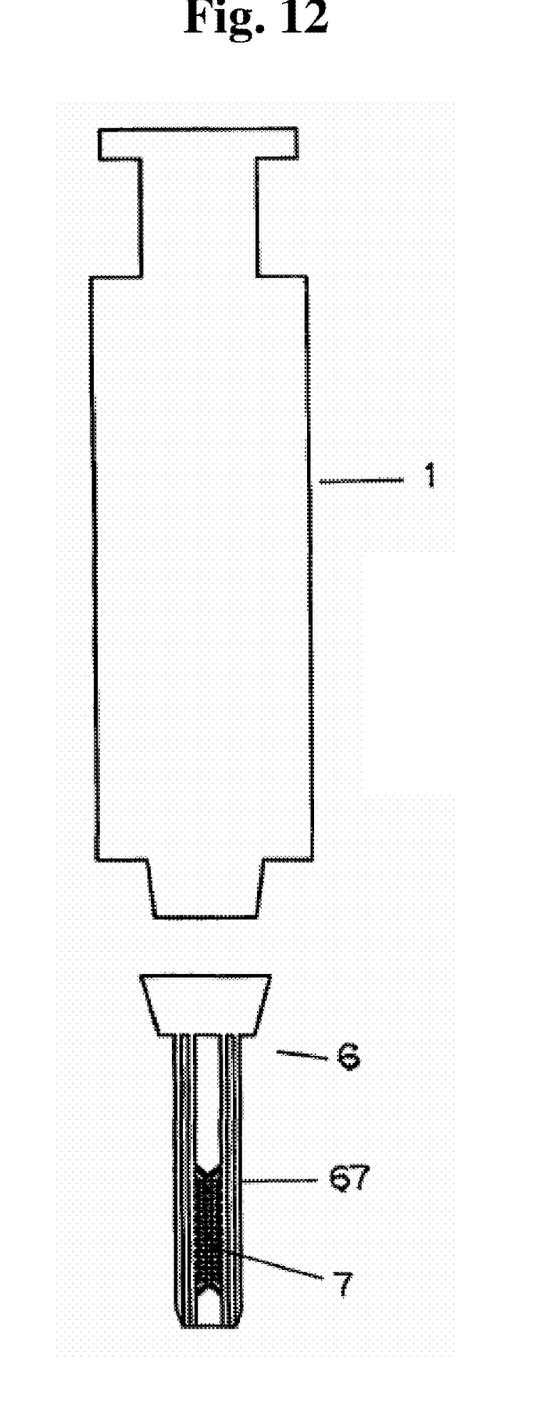
FIG. 12 illustrates the use of the above described other example.

Another example of the needle 6 will be described with reference to FIG. 11 and FIG. 12. An outer cylinder 67 made of a metal such as stainless steel or other materials having a certain strength is formed outside the needle 6 to protect the needle 6.

Therefore, if the well plate is covered with a film for example, the needle 6 can penetrate the film when the needle 6 is inserted into the well, so that the needle 6 is surely protected and prevented from accidents such as breakage.

Example of Synthesis

Example 4

A skeletal body having a $SiO_2$ skeleton and having 2 μm macropores, whose diameter is 1 mm and whose length is 25 mm, is formed within a syringe by an ordinary method, then the whole of the syringe is dipped in 200 mL of a 5% aqueous solution of hydrochloric acid and refluxed for 8 hours at 120° C. to be activated. After the activation, the skeletal body is inserted into a Teflon tube, where the skeletal body is heated and shrank to allow for passing a liquid therethrough. 9 mL of tetraethoxysilane, 11 mL of water, 4 mL of methanol, 4 mL of dimethylformamide, and 4 mL of aqueous ammonia are stirred for 10 minutes at 0° C. under a reduced pressure to be activated. This liquid is made to flow through the above-described skeletal body for 10 minutes at a rate of 0.5 mL/min. The skeletal body is sealed so that air is shut off. A temperature as a whole is increased to 60° C. at a temperature rising rate of 20° C. per minute and held at 60° C. for 6 hours to be gelatinized while bonding it to the inner surfaces of the macropores. The temperature is decreased to a room temperature, then 10 mL of 0.01 N aqueous solution of sodium hydroxide is made to continuously flow therethrough at a rate of 0.1 mL/min. to eliminate the unreacted liquid. The skeletal body is sealed and subjected to aging for 6 hours at 80° C. in order to make a porous body having micropores. By the use of a nitrogen adsorption measurement method, it has been recognized that the surface area is 400 m$^2$/g and the pore size is 20 nm. The temperature is decreased to a room temperature, the porous body is washed with 5 mL of water, 5 mL of acetone, and 20 mL of hexane in this order at a rate of 0.2 mL/min. In this case, it is recommended that the ratio of macropores and miropores is 0.1 to 200, and the capacity ratio between a macropore phase and a micropore phase is 0.1 to 2000.

Example 5

Another example of the present invention will now be described.

First, a gel having a solvent rich phase which becomes a huge vacancy about 100 nm or more is prepared through a sol-gel process, and the bulky gel is dipped in aqueous solutions having various compositions without the gel being ground. Then the gel is transformed into a porous body of a double pore type having a narrow pore distribution such that the inner wall of the huge vacancy is up to about 20 nm. According to this method, an inorganic porous body can be made which can substantially reproduce the porous structure having a desired mean pore size and a narrow distribution rather than a broader pore size distribution which has not been avoidable in the conventional porous body. Therefore, two kinds of pores, that is, a huge vacancy and a pore referred to as a double pore structure is realized.

First, 0.70 g of polyethylene oxide which is a water soluble macromolecule is dissolved in 10 g of 0.001 N aqueous solution of acetic acid, to which 5 ml of tetramethoxysilane is added while stirring the solution in order to perform a hydrolysis reaction. After stirring the solution for several minutes, the obtained clear solution is transferred into a closed vessel and kept in a thermostat at 40° C., then the solution was gelatinized after 40 minutes had passed.

The gelatinized sample was further subjected to aging for several hours and dipped in a 0.1 N aqueous solution of ammonia at 40° C. for three days or more. The solution was replaced with new one every day. In this case, the pH value of the aqueous solution of ammonia was about 10. After this treatment, the gel was dried for 6 hours and heated to 600° C. at a temperature rising rate of 100° C./h. This resulted in a porous body made of amorphous silica. It was confirmed by an electron microscope and mercury penetration measurement that through-holes whose central diameters were uniformly about 1.6 μm (=1600 nm) were present in the obtained porous body with the through-holes being entangled to form a three dimensional network. And it was also confirmed that a great number of pores whose diameters were about 10 nm existed at the inner wall of the through-holes by the nitrogen adsorption measurement. In addition, the porous body was manufactured under the same conditions as described above except that the temperature when the porous body was dipped in the ammonia solution was changed to 25° C. or 60° C. As a result of the manufacture, the vacancy distribution was not changed, but the mean pore size measured by the nitrogen adsorption method was changed to about 6 nm or 13 nm respectively.

It was found that the larger pore size can be obtained as the temperature when the porous body was dipped in the ammonia solution becomes higher, thus it was also confirmed that the pore size can be controlled by the temperature.

Example 6

Water soluble organic macromolecules are dissolved in an acidic aqueous solution, to which metal alkoxides having hydrolyzable functional groups and oligomers thereof are added for inducing a hydrolytic reaction, then after the products are solidified, drying and heating or a solvent substitution is performed. An open structure is thus formed with the organic macromolecule phase and the silica polymer phase entangled.

First, sodium polystyrene sulfonate which was a polymeric metallic salt was dissolved in 5.51 g of 1N aqueous solution of nitric acid to prepare a 20% solution by weight. 5 ml of methanol was added to this solution to make a homogeneous solution, then 5 ml of tetramethoxysilane was dropped therein over about one minute to induce a hydrolytic reaction. After the solution was stirred for several minutes, the obtained clear solution was transferred into a closed vessel and kept in a thermostat at 40° C., then the solution was gelatinized after about 20 hours had passed. The gelatinized sample was further subjected to aging for several days and dried at 60° C., then the sample was heated to 500° C. at a temperature rising rate of 100° C./h. This resulted in a porous body made of amorphous silica. The decomposition products of sodium polystyrene sulfonate was washed with water and finally subjected to a thermal treatment for 2 hours at 800° C. A porous silica glass, in which pores whose sizes were uniformly about 5 μm existed in an open structure, was obtained.

INDUSTRIAL APPLICABILITY

According to claim 1 of the present invention, an analyte can be extracted by solid-phase extraction in which the component is simply passed through a needle, so that the analyte can be concentrated by an extremely simple procedure. In addition, when the sample passes through the needle, the analyte is diffused and retained in pores of a porous body formed across an overall diameter of the needle with an extremely high degree of efficiency, and reduction in time required for concentration can be realized. Further, desorption of the analyte, effected by using a solvent, requires only a small amount of solvent. Also, desorption effected by heating is extremely simple and efforts can be saved.

The sample passes through the porous body having an integral and so-called monolithic structure, so that a sample capacity is larger than that in the case of a capillary column and the distribution resistance is lower than that in the case of a column which is packed with particulate substances. Actually, a pressure of about 10 MPa or more is applied for passing the sample through a 3μ ODS silica gel whose inner diameter was 0.3 mm×10 mm at a rate of 200 μL/min, but when a column having a so-called monolithic structure whose size was the same as described above was used, the applied pressure was 0.2 MPa. Further, a time required for the analyte to reach a distribution equilibrium can be reduced in comparison with a fiber for SPME, so that such reduction in time allows for conducting an efficient analysis.

According to claim 2 of the present invention, in addition to the above-described effects of claim 1, a syringe-usable auto injector is easily used and an apparatus is easily automated.

According to claim 3 of the present invention, in addition to the above described effects of claim 1, a needle and a syringe containing a sample and an analyte is easily replaced with new ones by making the needle attachable and detachable, so that the treatment of a many kinds of and/or a large amount of samples and analyte is extremely smoothly conducted, and complete automation of the analysis can be realized.

According to claim 4 of the present invention, the same effect as in the case of claim 3 is produced in addition to the effects of claim 1. Further, according to claim 5, a sample tip can be utilized for easily concentrating and purifying the sample in addition to the effects of claim 4. According to claim 6, a sample tip is attachable and detachable, so that only a sample tip can be sequentially discarded, so that a plurality of samples can be subjected to a pre-treatment quickly and without contamination.

According to claim 7, an outside of the needle is protected by an outer cylinder, so that the needle can be easily inserted through a well of a multi well plate even when the multi well plate is covered with a film and the needle can be protected. This is effective for automating the insertion of the needle through the well. According to claims 8 and 9, a separation mode is simplified and an exact separation is performed, so that an improvement in analytical performance can be effected. According to claims 10 and 11, a surface area of a porous body can be increased and a property which is different from a skeletal body can be imparted to the porous body, so that the porous body can be available for a wide variety of samples having various properties.

What is claimed is:

1. A method for performing solid-phase-micro extraction of a component present in a sample, which uses a syringe having a cylinder and a plunger slidable within the cylinder, a tip of the syringe being provided with a needle and the needle being provided with a monolithic structure having an open cell porous body forming at least one pore having a structure communicating from an upper end to a lower end of the porous body, the at least one pore having a distribution of open cell structures which is substantially uniform, wherein the porous body extends across the entire inner diameter of the needle, comprising the steps of inserting the needle into the sample, passing the sample through the needle to retain an analyte within the porous body, and desorbing the retained analyte from the porous body.

2. The method for performing solid-phase-micro extraction according to claim 1, wherein the porous body is a single pore.

3. The method for performing solid-phase-micro extraction according to claim 1, wherein the porous body is a double pore.

4. An apparatus for performing solid-phase-micro extraction of a component present in a sample, comprising a syringe having a cylinder and a plunger slidable within the cylinder, a tip of the syringe being provided with a needle and the needle being provided with a monolithic structure having an open cell porous body forming at least one pore having a structure communicating from an upper end to a lower end of the porous body, the at least one pore having a distribution of open cell structures which is substantially uniform, wherein the porous body extends across the entire inner diameter of the needle, such that the sample is retained within the porous body when the sample passes through the needle and subsequently desorbed from the porous body.

5. The apparatus for performing solid-phase-micro extraction according to claim 4, wherein the porous body is a single pore.

6. The apparatus for performing solid-phase-micro extraction according to claim 4, wherein the porous body is a double pore.

7. A method for performing solid-phase-micro extraction of a component present in a sample, comprising the steps of providing a syringe having a cylinder and a plunger slidable within the cylinder, a tip of the syringe being provided with a needle and the needle being provided with a monolithic structure having an open cell porous body forming at least one pore having a structure communicating from an upper end to a lower end of the porous body, the at least one pore having a distribution of open cell structures which is substantially uniform, wherein the porous body extends across the entire inner diameter of the needle, wherein at least a portion of the needle within which the porous body is formed is attachable and detachable from the syringe or the needle, and wherein an analyte is retained within the porous body by passing a sample through the porous body when the sample passes through the needle.

8. An apparatus for performing solid-phase-micro extraction of a component present in a sample, comprising a syringe having a cylinder and a plunger slidable within the cylinder, a tip of the syringe being provided with a needle an the needle being provided with a monolithic structure having an open cell porous body forming at least one pore having a structure communicating from an upper end to a lower end of the porous body, the at least one pore having a distribution of open cell structures which is substantially uniform, wherein the porous body extends across the entire inner diameter of the needle, and that the entire needle or at least a portion of the needle within which the porous body is formed is selectively attachable and detachable with respect to the syringe or the needle.

9. A needle for selective attachment and detachment with a syringe or for use with a syringe, comprising a needle body and a monolithic structure having an open cell porous body forming at least one pore having a structure communicating from an upper end to a lower end of the porous body, the at least one pore having a distribution of open cell structures which is substantially uniform, wherein the porous body extends across the entire inner diameter of the needle and extending along at least a portion of the length of the needle.

10. The needle according to claim 9, wherein the needle is a sample tip.

11. The needle according to claim 9, wherein an outside of the needle is provided with an outer cylinder.

* * * * *